United States Patent [19]

Smiley

[11] 4,399,220
[45] Aug. 16, 1983

[54] STABILIZING LACTOBACILLI

[75] Inventor: Martin B. Smiley, Blonay, Switzerland

[73] Assignee: Societe d'Assistance Technique pour Produits Nestle S.A., Lausanne, Switzerland

[21] Appl. No.: 16,085

[22] Filed: Feb. 28, 1979

[30] Foreign Application Priority Data

Mar. 16, 1978 [CH] Switzerland .......................... 2861/78

[51] Int. Cl.³ ......................... C12N 1/00; C12N 1/20; C12N 15/00; C12P 7/56
[52] U.S. Cl. .................................... 435/139; 435/172; 435/243; 435/253; 435/317
[58] Field of Search ............... 435/139, 172, 853, 243, 435/245, 253, 317, 244

[56] References Cited

U.S. PATENT DOCUMENTS 2,768,116 10/1956 György et al. ................. 435/853 X
2,770,573 11/1956 György et al. ....................... 195/28
3,813,316 5/1974 Chakrabarty ................... 435/172 X

OTHER PUBLICATIONS

Smiley et al., Chemical Abstracts 89:20181a (1978).
Matteuzzi, Canadian Journal of Microbiology, 18, 1893–1895 (1972).
Bergey's Manual of Determinative Bacteriology, 8th Ed., Buchanan Editor, The Williams & Wilkins Co., Baltimore, 582 (1974).

Primary Examiner—Esther M. Kepplinger
Attorney, Agent, or Firm—Vogt & O'Donnell

[57] ABSTRACT

A process for producing a stable culture of a microorganism of the genus Lactobacillus containing at least one extrachromosomal genetic element which, on the one hand, stimulates its ability to produce lactic acid from lactose and which, on the other hand, controls its ability to metabolize N-acetyl-D-glucosamine, which comprises cultivating the microorganism in a nutrient medium of which the principal source of assimilable carbon is N-acetyl-D-glucosamine.

2 Claims, No Drawings

STABILIZING LACTOBACILLI

This invention relates to a process for producing a stable culture of a microorganism of the genus Lactobacillus having at least one extrachromosomal genetic element which, on the one hand, stimulates its ability to produce lactic acid from lactose and, on the other hand, controls its ability to metabolise N-acetyl-D-glucosamine.

A significant problem encountered in the manufacture of milk-based products, such as cheeses and yoghurts for example, lies in the instability of the strains of microorganisms cultivated for and used in the manufacture of these products, particularly those microorganisms which produce lactic acid from lactose, for example microorganisms of the genus Lactobacillus. This is because the ability of so-called lactic microorganisms to produce lactic acid from lactose, which will be referred to hereinafter as their "activity" or "lactic acid production capacity", is known to diminish as a function of time.

Certain specialists have studied the mechanism behind the production of lactic acid by means of genetics. Thus, it is now known that a plasmide is responsible for the fermentation of lactose by *Streptococcus lactis* and that plasmides may be involved in the metabolism of lactose by certain Lactobacilli.

Plasmides are extrachromosomal genetic elements in the form of a circular molecule of desoxy ribonucleic acid (DNA) of which the weight is equivalent to a few per thousand or to tens per thousand of the weight of the chromosome of the microorganism.

However, unless a plasmide is completely responsible for the fermentation of lactose by a microorganism, in which case it is sufficient to cultivate the microorganism in milk to retain its activity, the present level of knowledge can hardly be put to use in industry for stabilising the activity of lactic microorganisms.

It is also known that different strains of the same species of microorganism can differ considerably in their lactic acid production capacity. This is particularly true of the microorganism *Lactobacillus helveticus* sub-species *jugurti*. This microorganism is used in the production of Gruyere, Emmenthal and Parmesan. In other words, it would involve more than just an academic exercise to find a solution to this problem and to be able to guarantee maximum activity of each strain.

The present invention provides a solution to this problem.

The present invention provides a process for producing a stable culture of a microorganism of the genus Lactobacillus containing at least one extrachromosomal genetic element which, on the one hand, stimulates its ability to produce lactic acid from lactose and which, on the other hand, controls its ability to metabolise N-acetyl-D-glucosamine, which comprises cultivating the microorganism in a nutrient medium of which the principal source of assimilable carbon is N-acetyl-D-glucosamine.

In the context of the invention, the principal source of assimilable carbon is understood to be the determining source without which the microorganism could not develop, which does not exclude the presence of other "minor" sources which would be added to the medium with a source of oligoelements and vitamins, such as yeast extract for example.

It was found during an indepth comparative study of the properties of two strains of the same species of Lactobacillus, namely *Lactobacillus helveticus,* sub-species *jugurti,* one of which had a much higher lactic acid production capacity than the other, that this high capacity was due to the presence of a plasmide of 13.17 kilobases (kb). This plasmide was absent from the low-capacity strain. It was found that this plasmide does not control the ability of the strain to produce lactic acid from lactose, but stimulates this ability, in other words it controls a factor stimulating the production of lactic acid, this production, whether stimulated or not, high or low, being controlled by genes situated on the chromosome. It was also found that this plasmide completely controls the ability of the microorganism to metabolise N-acetyl-D-glucosamine. In this way, Applicants succeeded in demonstrating the reason for which two strains of the same species do not have the same capacity for degrading lactic acid, and in finding a means eminently suitable for use on a commercial scale for cultivating and maintaining stable highly active strains of these microorganisms.

In effect, plasmides are capable of being lost during the division of cells. On the one hand, the replication of the chromosomes is not necessarily accompanied by replication of the plasmides, whilst on the other hand, the plasmides resulting from replications are not necessarily distributed in equal parts among the cells arising out of cell divisions. However, if the cells are cultivated on a medium of which the carbon source can only be exploited through the plasmide, the cells without plasmides will not be viable and will disappear accordingly in favour of the cells containing plasmide.

Accordingly, the practical application of the process according to the invention involves the use of a microorganism of the genus Lactobacillus which contains at least one extrachromosomal genetic element, in other words at least one plasmide, which on the one hand stimulates its ability to produce lactic acid from lactose and which on the other hand controls its ability to metabolise N-acetyl-D-glucosamine. The microorganism is preferably *Lactobacillus helveticus* of the sub-species *jugurti* S 36-2 which may be obtained at the Institute of Agronomic Microbiology of the University of Bologna in Italy.

The microorganism may be maintained or conserved by transferring it monthly to an aqueous medium with a dry matter content of 5 to 10% by weight containing an adequate source of assimilable nitrogen, salts, oligoelements and vitamins as well as N-acetyl-D-glucosamine as the principal source of assimilable carbon, this medium having been sterilised before the transfer, for example by heating in an autoclave for 30 minutes to a temperature of 115° C. The inoculated medium may be incubated at a temperature favourable to the growth of the microorganism, for example 40° to 42° C., until its optical density corresponds to the logarithmic half-growth for example. Between the transfers, it may be kept at a temperature sufficiently low to prevent the microorganism from multiplying, for example 5° to 10° C. When it is desired to produce a quantity of microorganism sufficient for the commercial production of cheese or yoghurt for example, it is possible to start with the above mentioned cultures, to cultivate them and to transfer them the necessary number of times, for example three to four times, at a temperature favourable to their growth in milk. The transfers may be made in quantities of from 0.5% to a few % and preferbly in a quantity of 1% by volume of the culture to be transferred relative to the volume of the milk to be inoculated.

The invention is illustrated by the following Example in which the percentages quoted represent % by weight.

EXAMPLE

On the other hand, two strains of *Lactobacillus helveticus*, a sub-species *jugurti*, respectively numbered S 13-8 and S 36-2, obtained from the Institute of Agronomic Microbiology of the University of Bologna in Italy, are separately cultivated in a suspension of 10% of powder-form skimmed milk and 0.1% of yeast extract in water, the suspension having been sterilised for 30 minutes at 115° C. in an autoclave. After incubation for 8 hours at 42° C., the strain S 13-8 has produced 1.5% of lactic acid in the suspension and the strain S 36-2 2.4%.

On the other hand, the strain S 36-2 is grown on MRS medium (J. C. de Man, M. Rogosa and M. F. Sharpe, J. Appl. Bact. 23, 130–135 (1960)) for Lactobacilli. Samples of this culture are transferred to fresh MRS medium to which 7 µg/ml of acriflavine have been added. The cultures thus transferred are incubated for 24 hours, sub-cultured on MRS medium solidified by the addition of 1.5% of agar and incubated in an atmosphere of hydrogen and $CO_2$. Individual colonies are isolated.

A certain number of samples of the strain S 36-2, which have not undergone the treatment with acriflavine, and the above mentioned colonies which have undergone the treatment with acriflavine are then individually cultivated in a modified MRS medium having the following composition:

| | |
|---|---|
| N—acetyl-D-glucosamine | 10 g |
| polypeptone | 10 g |
| yeast extract | 5 g |
| Tween 80* | 1 ml |
| $K_2HPO_4$ | 2 g |
| $CH_3COONa.3H_2O$ | 5 g |
| diammonium citrate | 2 g |
| $MgSO_4.7H_2O$ | 0.2 g |
| $MnSO_4.4H_2O$ | 0.05 g |
| distilled water | 1 liter |

*(polyoxyethylene sorbitan monooleate)

It is found that approximately 60% of these colonies are incapable of growing on the above medium where the N-acetyl-D-glucosamine is the principal source of assimilable carbon, whereas only 1% of the reference samples is unable to grow on that medium. In an aqueous suspension of 10% of powder-form skimmed milk and 0.1% of yeast extract, it is verified that the colonies which are unable to metabolise the N-acetyl-D-glucosamine produce quantities of lactic acid of from 1.3% to 1.6%, i.e. as much as the strain S 13-8, over a period of 8 hours. By contrast, almost all the reference samples are capable of growing on the modified MRS medium and in 8 hours produce from 2.3 to 2.6% of lactic acid on the medium of powder-form skimmed milk and yeast extract. This property remains intact as long as these samples are cultivated or maintained on the modified MRS medium.

By suitable techniques of hydrolysis, separation by centrifuging under a density gradient of ClCs-ethidium bromide and electron microscopy, it can be verified that it is a plasmide of 13.17 kb which is present in the strain S 36-2, absent from the strain S 13-8 and neutralised in the strain S 36-2 treated with acriflavine, which is responsible on the one hand for the increase in the production of lactic acid from approximately 1.5% to approximately 2.4%, such as determined above, and on the other hand for the metabolisation of the N-acetyl-D-glucosamine.

We claim:

1. A process for producing a stable culture of a microorganism of the genus Lactobacillus containing at least one extrachromosomal genetic element which, on the one hand, stimulates its ability to produce lactic acid from lactose and which, on the other hand controls its ability to metabolise N-acetyl-D-glucosamine, which comprises cultivating the microorganism in a nutrient medium of which the principal source of assimilable carbon is N-acetyl-D-glucosamine.

2. A process as claimed in claim 1, wherein the microorganism is *Lactobacillus helveticus* of the subspecies, *jugurti* obtainable under No. S 36-2 from the Institute of Agronomic Microbiology of the University of Bologna in Italy.

* * * * *

UNITED STATES PATENT AND TRADEMARK OFFICE
CERTIFICATE OF CORRECTION

PATENT NO. : 4,399,220
DATED : August 16, 1983
INVENTOR(S) : Martin B. Smiley

It is certified that error appears in the above—identified patent and that said Letters Patent is hereby corrected as shown below:

At Column 3, line 20, "S 36-22.4%" should read -- S 36 - 2 2.4 % --.

Signed and Sealed this

Tenth Day of January 1984

[SEAL]

Attest:

GERALD J. MOSSINGHOFF

*Attesting Officer*     *Commissioner of Patents and Trademarks*